United States Patent [19]

Anderson et al.

[11] Patent Number: 4,918,198
[45] Date of Patent: Apr. 17, 1990

[54] N-(PYRROLIDONYALKYL)-N-ACYL TAURINE SURFACTANTS

[75] Inventors: Lowell R. Anderson, Morristown; Mohamed M. Hashem, Wayne; Robert B. Login, Oakland, all of N.J.

[73] Assignee: GAF Chemicals Corporation, Wayne, N.J.

[21] Appl. No.: 399,187

[22] Filed: Aug. 28, 1989

[51] Int. Cl.$^4$ .............................................. C07D 207/27
[52] U.S. Cl. ..................................................... 548/550
[58] Field of Search ........................................ 548/550

[56] References Cited

PUBLICATIONS

Sidgwick, "The Organic chemistry of Nitrogen", Oxford, Eng. Clarendon Press, 1937, pp. 138 & 139.

*Primary Examiner*—David B. Springer
*Attorney, Agent, or Firm*—Walter Katz; Marilyn J. Maue; Joshua J. Ward

[57] ABSTRACT

This invention provides novel and useful surfactants having the formula:

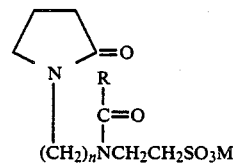

where
R is a long chain fatty acid alkyl group, saturated or unsaturated, e.g. having from 8-22 carbon atoms, as for example, lauryl, stearyl, oleyl, palmityl, myristyl, and mixtures such as coco, tallow, etc.,
M is a metal ion, preferably an alkali metal such as sodium, potassium, etc., and
n is 1-6.

12 Claims, No Drawings

N-(PYRROLIDONYALKYL)-N-ACYL TAURINE SURFACTANTS

BACKGROUND OF THE INVENTION

1. Field of the Invention

This invention relates to surfactants, and more particularly, to surfactants with excellent water solubility and complexation ability for metals and drugs.

2. Description of the Prior Art

The reaction of amines with sodium isethionate has been used extensively to prepare intermediates for Igepon® (GAF Corp.) surfactants. Such intermediates then are acylated with a long chain acyl halide to provide the desired surfactant.

3. Objects of the Invention

An object of this invention is to provide new and improved Igepon® surfactants which exhibit excellent water solubility and complexation ability.

SUMMARY OF THE INVENTION

This invention provides novel and useful N-(pyrolidonylalkyl) N-acyl taurine surfactants having the formula:

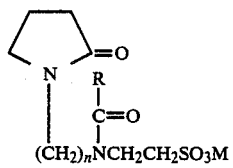

where R is a long chain fatty acid alkyl group, saturated or unsaturated, having, preferably, from 8–22 carbon atoms, e.g. lauryl, stearyl, oleyl, palmityl, myristyl, and mixtures such as coco, tallow, etc.

M is a metal ion, e.g. an alkali metal such as sodium, potassium, etc.

In the preferred form of the invention n=2 and M is sodium.

The invention also provides N-(pyrrolidonylalkyl) taurine intermediates for use in the manufacture of such surfactants having the formula:

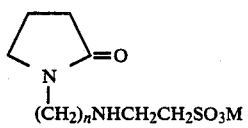

where M and n are defined above.

A suitable process for making the intermediate compound and surfactant of the invention is disclosed herein.

DETAILED DESCRIPTION OF THE INVENTION

In accordance with the present invention, the surfactants herein are made in a two-step process. The first step involves the reaction of excess aminoalkyl pyrrolidone with sodium isethionate to produce a sodium N-(pyrrolidonylalkyl) taurine intermediate. The second step comprises acylation of the intermediate with a long chain (fatty acid) acyl halide having an alkyl group containing about 8–22 carbon atoms, which group may be saturated or unsaturated.

In the following reaction scheme X is a suitable halide, e.g. chloride:

Step One

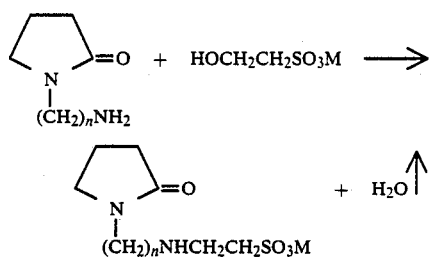

Step Two

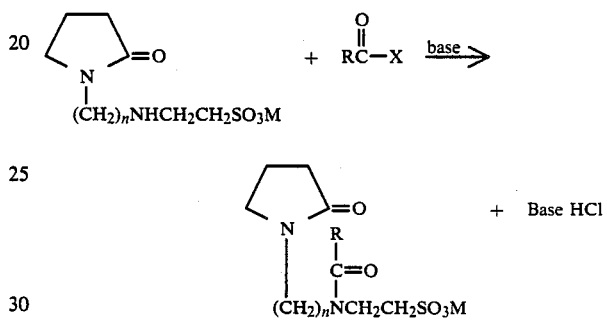

In the first step of the process, condensation is carried out using a molar excess of aminoalkyl pyrrolidone over sodium isethionate, usually about a 2:1 to 6:1 molar excess. The reaction is run at a temperature of about 200° to 230° C., at atmospheric pressure, for about 6–24 hours, while water is continuously removed. The intermediate compound is obtained after distillation of volatile materials from the reaction mixture. The yield of the intermediate is substantially quantitative and it may be used for subsequent reaction without further purification.

In the second step of the process, acylation of the intermediate is effected under alkaline conditions, e.g. a pH of 9–10, at a temperature of about 20°–30° C., in water as a solvent, using a molar ratio of intermediate to acid chloride of about 1:2, preferably about 1:1.5.

The invention now will be described with reference to the following examples.

EXAMPLE 1

Preparation of N-(Pyrrolidonylethyl) Taurine, Sodium Salt

Aminoethyl pyrrolidone (256.0 g, 2 moles) and sodium isethionate (74.0 g, 0.5 moles) were charged into a 500 ml, 4-necked round bottom flask equipped with an overhead stirrer, thermometer with controller, condenser (with Dean-Stark apparatus) and a nitrogen inlet. The mixture then was heated with stirring to a temperature near the boiling point of the aminoethyl pyrrolidone/sodium isethionate reaction mixture, suitably about 228° C. Heating and stirring was continued for 6–24 hours. Approximately 7 g of water was recovered in the trap (theory=9 g). Then 10 g of the reaction material was subjected to a Kugelrohr distillation (180° C.) to remove volatiles. The residue constituted 98.0% of theory for the desired product. Titration of the Kugelrohr residue with 0.1N HCl was 99.3% of theory for the title compound. Infrared and nuclear magnetic resonance spectra data also were consistent with the named compound.

EXAMPLE 2

Preparation of N-(Pyrrolidonylethyl) N-Lauryloyl Taurine, Sodium Salt

A liquid charge was made to a 100 ml. beaker of 25.8 g of the intermediate of Example 1 and 26.3 g of water. Stirring was provided by a magnetic stirrer. A thermometer and a pH electrode was introduced in the vessel to monitor the solution. Lauroyl chloride (25.0 g) then was added from a dropping funnel with its stem below the surface of the liquid charge. The solution was initially adjusted to a pH of 9–10 with aqueous sodium hydroxide and was maintained in this range by further additions of base throughout the addition of the lauroyl chloride. The temperature of the reaction was maintained between 20°–30° C. by adjusting the rate of addition of lauroyl chloride. After completion of the addition, the pH was lowered to 6.0. The product then was rotary evaporated to remove water. A light yellow solid was obtained which was dissolved in methylene chloride and filtered to remove sodium chloride. Evaporation of the filtrate produced a salt free solid product. The infra-red and nuclear magnetic resonance spectra of the product was consistent with the named compound. The purity was 85%.

EXAMPLE 3

The procedure of Example 2 was repeated using oleoyl chloride in place of lauroyl chloride, with similar results.

EXAMPLE 4

The surfactants of Examples 2 and 3 were tested for lime soap dispersant properties, water solubility and complexation capability, and were found to be very effective in respect to these criteria for new and useful surfactant materials for commercial application.

While the invention has been described with particular reference to certain embodiments thereof, it will be understood that changes and modifications may be made which are within the skill of the art. Accordingly, it is intended to be bound only by the appended claims.

What is claimed is:

1. A surfactant having the formula:

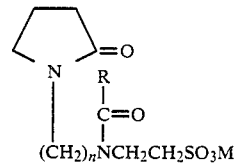

where R is a alkyl group, saturated or unsaturated, having from 8–22 carbon atoms,
M is a metal ion, and
n is 1–6.

2. A surfactant according to claim 1 wherein n is 2.

3. A surfactant according to claim 1 wherein M is an alkali metal.

4. A surfactant according to claim 2 wherein M is sodium.

5. A surfactant according to claim 1 wherein R is selected from lauryl, stearyl, oleyl, palmityl, myristyl, coco and tallow.

6. A surfactant according to claim 1 which is sodium N-(pyrrolidonylethyl) N-lauroyl taurine.

7. A surfactant according to claim 1 which is sodium N-(Pyrrolidonylethyl) N-oleoyl taurine.

8. An intermediate compound for making the surfactant of claim 1 having the formula:

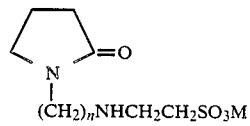

where n and M are defined in claim 1.

9. An intermediate compound according to claim 8 wherein n is 2.

10. An intermediate compound according to claim 8 wherein M is an alkali metal.

11. An intermediate compound according to claim 8 wherein M is sodium.

12. An intermediate compound according to claim 8 which is sodium N-(pyrrolidonylethyl) taurine.